United States Patent [19]
Fuller et al.

[11] Patent Number: 6,127,159
[45] Date of Patent: Oct. 3, 2000

[54] MITOFUSIN GENES AND THEIR USES

[75] Inventors: Margaret T. Fuller, Stanford, Calif.; Karen G. Hales, Durham, N.C.

[73] Assignee: The Board of Trustees of the Leland Stanford Junior University, Palo Alto, Calif.

[21] Appl. No.: 09/090,808

[22] Filed: Jun. 4, 1998

Related U.S. Application Data

[60] Provisional application No. 60/048,961, Jun. 6, 1997.

[51] Int. Cl.⁷ ........................................... C12N 9/12
[52] U.S. Cl. .................. 435/194; 435/183; 435/196; 424/94.1
[58] Field of Search .................. 424/94.1; 435/194, 435/196, 252.2, 254.2, 320.1, 365, 419

[56] References Cited

FOREIGN PATENT DOCUMENTS

95/06764  3/1995  WIPO .

OTHER PUBLICATIONS

Accession No. AA052806.
Accession No. AA010217.
Accession No. AA155601.
Accession No. AA199015.
Accession No. AA212845
Accession No. AA248083.
Accession No. D16943.
Accession No. H58349.
Accession No. R20140.
Accession No. T06373.
Accession No. T37724.
Accession No. W49736.
Accession No. Z36048 Y13134.
Kawano, Shigeyuki, et al., "Sexuality Of Mitochondra: Fusion, Recombination, and Plasmids," *International Review of Cytology* (1995) vol. 161:49–110.

Larsson, Nils–Göran, et al., "Molecular Genetic Aspects Of Human Mitochomdrial Disorders," *Annu. Rev. Genetics* (1995) vol. 29:151–178.

Bashkin, James K., et al., "Robozyme Mimics as Catalytic Antisense Reagents," *Applied Biochemistry and Biotechnology* (1995) vol. 54:43–56.

Furth, Priscilla A., et al., "Gene Transfer Into Somatic Tissues By Jet Injection," *Analytical Biochemistry* (1992) vol. 205:365–368.

Tang, De–chu, et al., "Genetic Immunization Is A Simple Method For Eliciting An Immune Response," *Nature* (Mar. 12, 1992) vol. 356:152–154.

Wagner, Richard W., et al., "Potent and Selective Inhibition Of Gene Expression By An Antisense Heptanucleotide," *Nature Biotechnology* (Jul. 1996) vol. 14:840–844.

The 1992 Sigma Catalog, Published by the Sigma chemical Company, Jan. 1, 1992, see p. 62, product No. A7627.

*Primary Examiner*—Ponnathapu Achutamurthy
*Assistant Examiner*—Manjunath N. Rao
*Attorney, Agent, or Firm*—Pamela J. Sherwood; Bozicevic, Field & Francis

[57] ABSTRACT

Mitofusin genes and encoded polypeptides are provided, including the Drosophila Fzo protein and its homologs from insects, other invertebrates, yeast, and vertebrates including mouse and humans. Motifusins are large predicted GTPases with a predicted trans-membrane domain, coiled-coil regions, and a C-terminal region showing a high pI characteristic of mitochondrial matrix proteins. The mitofusins are the first known protein mediator of mitochondrial fusion, and -mediate developmentally regulated post-meiotic fusion of mitochondria. Missense mutations that alter conserved residues required for GTP binding in other GTPases inhibit the in vivo fusogenic activitiy of Fzo but do not affect its localization.

14 Claims, 5 Drawing Sheets

```
MAESDSGESTSSVSSFISSSSSSRLSEFVDAKTELQDIYHDLSNYLSNFLTILEETVLLKDRQMLEHLCAFSSRVEAIAKVLSRDRMKVA    90
           T

FFGRTSNGKSAVINALLHEKILPSAMGHTTSCFCQVQANGSNETEHVKVEQEDEHMELSALSQLASAHSPGALKPSTLLQVNMAKNRCSI   180
         G1                            G2

LDYDVVLMDTPGVDVTAQLDDCLDSYCMDADVFILVLNAESTVSRVERQFFKDVASKLSRPNLFILNNRWDKASSLEPEMEQKVKDQHME   270
          G3                                                              G4

RCVNLLLVDELGVYSTAQEAWERIYHVSALEALHIRNGQITNPSGQTQQRYQEFLRFENDFSNCLAVSALKTKFGPHLLSAQKILNQLKST   360

LICPFIEKVSRLIDENKERRANLNAEIEDWLILMQEDREALQYCFEELTEMTQRVGRCVLSDQIKTLIPSSVLSFSQPFHPEFPAQIGQY   450
                              *****************

QRSLCAHLDKLLEDRVLQCLSIPLQREILDIEKEIGLPIAENSCDWQLIYGLDCQSYMSDFQPDLRFRFSLGFTALWHRLEGNLPLHASP   540

FRIQKLQNGHKKCSPLPPLVNGNHWQMLESLVKSKGSLGTVLLSAMAIRSFNWPIVLILGGLVGSFYIYEYAAWTTAAQERSFKSQYARL   630
                                ************ ***************

LQQRLRSDVQQTVSGFELQLRQHLATVRNCWEAQSNETLNDLNVRTAELTKQIQSMEVLQLSLKKFRDKGQLLASRLGDFQETYLTKS    718
                                            **************************
```

```
                            G1                                              G2
Fzo           FSSRVEAIAKVLSRDRMKVAFFGRTSNGKSAVINALLHEKILPSAMGHTTSCFCQV-   127
C. elegans    IGDSIKTIMDTFQRDNMKVVFFGRTSNGKSTTINAMLHEKVLPQGMGHTTCCFLQV-   141
S. cerevisiae VTNHLNALKKRVDDVSSKVFITGDVNTGKSALCNSLLKQRLLPEDQLPCTNVFSEIL   228
C. saccharolyt. ------AGSIKEKIEKNAFYLVVLGQFKRGKSTLINYMLGANLLPTGVLPLISVITKIY  88
```

FIG. 2C

```
                              G3
H. sapiens Fzo    VRVFCPK----AKCALLRD----DLVLVDSPGTDVTT-ELDSWIDKFCLDADVFVLVA(69)
C. elegans       LQVNMAKN----RCSILDY----DVVLMDTPGVDVTA-QLDDCLDSYCMDADVFILVL  217
S. cerevisiae    LKVFHPKKSESGECRLLQN----DVVILDSPGVDLSP-EFDSWIDKHCLDADVFVLVS  239
C. saccharolyt.  LKIYIKDDKRPASTSLLRNGTVDISLIDSPGLNMDSLQTAEVMSR-QEEIDLVIFVV  341
                 LNK--------------------DVVIVDTPGIGSVYQHNTDVTYEFIDKSDAVVFVL  177
                                            G4
H. sapiens Fzo    NSESTLMNTEKHFFHKVNERLSKPNIFILNNRWDASAS-EPEYMEDVRRQHMERCLH(125)
C. elegans       NAESTVSRVERQFFKDVASKLSRPNLFILNNRWDKASSLEPEMEQKVKDQHMERCVN   274
S. cerevisiae    NAESTLTQAEKNFFLRVAKKLSKPNVFILNNRWDASAA-ETENIEDVKKQHLTRFRQ   295
C. saccharolyt.  NAENQLTLSAKEFISLASREKKL----MFFVVKKFDKIRD------------KQRCKELIL  386
                 SVDPPITEVEKQFLLKIAENVDK---IFFVINKSD-LTS------------KNEIEEIV-  221
```

FIG. 2F
```
         ************
Fzo      GNEWQMLESLVKSKGSLGTVLLSAMAIR    589
C. e.    MTQMVLTSAAFLANGSLGVLVVGGIVYK    640
H. s.    MITLVTGLASVTSRTSMGIIIVGGVIWK   (359)
S. c.    KIPTLTLYFLGSTKVVGNIILNGIKLSS    729
         ******************
Fzo      SFNWPIVLILGGLVGSFYIYEYAAWTTE    617
C. e.    AVGWRVIAVGGAAYAGLYAWERMRWNSG    668
H. s.    TIGWKLLSVSLTMYGALYLYERLSWTTA   (385)
S. c.    WSSLKKLSVPVIVVGSLLGLTYLINDLP    755
```
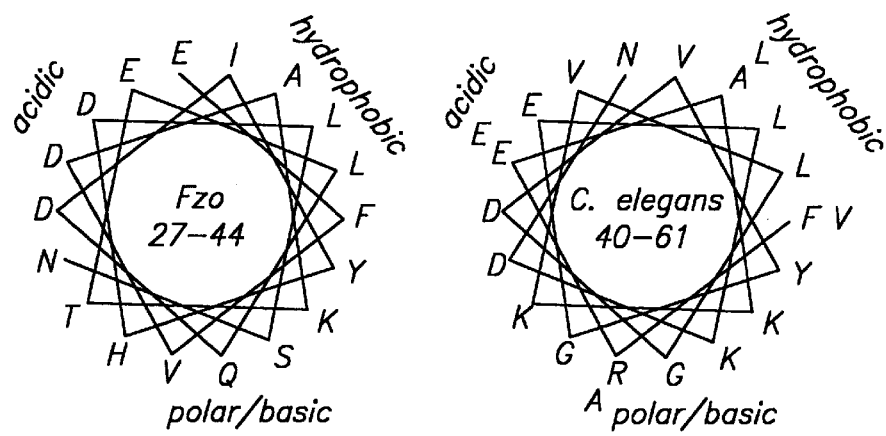
FIG. 2G
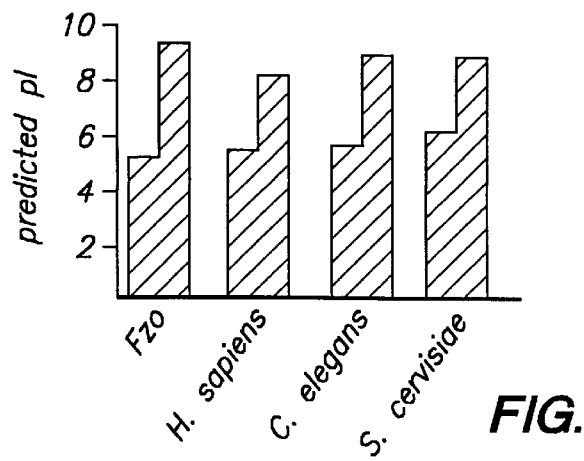
FIG. 2H

MITOFUSIN GENES AND THEIR USES

This application claims benefit of provisional application No. 60/048,961, filed Jun. 6, 1997.

INTRODUCTION

Accumulation of mutations in the mitochondrial genome has been proposed as an important contributor to aging and degenerative diseases. In several cases human mitochondrial disorders have been shown to be caused by mutations or deletions of mitochondrial DNA.

There is evidence for defects in energy metabolism, excitotoxicity, and for oxidative damage in the etiology of neurodegenerative diseases, including amyotrophic lateral sclerosis, Huntington's disease, Parkinson's disease, and Alzheimer's disease. It is likely that there is a complex interplay between these mechanisms. Mitochondrial DNA is particularly susceptible to oxidative stress, and there is evidence of age-dependent damage and deterioration of respiratory enzyme activities with normal aging. This may contribute to the delayed onset and age dependence of neurodegenerative diseases.

Mitochondria are dynamic organelles that undergo regulated fusion in many cell types. Analysis of serial sections from rodent skeletal muscle, lymphocytes, liver, spinal ganglion cells, and from the yeast *Saccharomyces cerevisiae* has shown that all the mitochondrial material of a cell can exist as a giant branched reticulum.

Specific protein mediators that act as biomechanical triggers and/or regulate specificity and timing of membrane fusion events have been identified in a wide variety of other cellular and subcellular contexts. The best characterized biomechanically acting fusogen is influenza virus hemagglutinin (HA) that mediates fusion of endocytosed viruses to cells. Regions resembling the HA fusion peptide exist in the ADAM family proteins, which are implicated in sperm/egg and myoblast fusion.

The identification of protein mediators of mitochondrial fusion and their possible role in maintenance of mitochondrial function and genomic integrity is of great interest for diagnosis, drug screening and potential therapeutic strategies, including targeted delivery of genes, proteins and molecules to existing mitochondria. If recombination between differently mutated mitochondrial DNA molecules allows restoration of a functional copy, the ability of mitochondria to fuse may play an important role in maintenance of mitochondrial genomes. Alternatively, fusion of mitochondria may allow complementation between two mutations in different genes in the mitochondrial genome, allowing restoration of mitochondrial function even in the absence of recombination.

Relevant literature

Larsson, N. -G., and D. A. Clayton. 1995. Molecular genetic aspects of human mitochondrial disorders. Annual Review of Genetics. 29:151–178.

Kawano, S., H. Takano, and T. Kuroiwa. 1995. Sexuality of mitochondria: fusion, recombination, and plasmids. Int. Rev. Cytol. 161:49–110.

SUMMARY OF THE INVENTION

Mitofusin genes and proteins are provided. As used herein, the term "mitofusin" indicates the Drosophila Fzo protein or any of its homologues from insects, other invertebrates, yeast, and vertebrates including mouse and humans. Motifusins are large predicted GTPases with a predicted trans-membrane domain, coiled-coil regions, and a C-terminal region showing a high pI characteristic of mitochondrial matrix proteins. The mitofusin Fzo is the first known protein mediator of mitochondrial fusion, and mediates developmentally regulated post-meiotic fusion of mitochondria in Drosophila spermatids.

BRIEF DESCRIPTION OF THE DRAWINGS

FIG. 2A shows the predicted amino acid sequence (single letter amino acid code) of the fzo gene product, with regions matching GTPase motifs in boldface and numbered G1–G4. Underlined region is the predicted transmembrane domain. Italics show the hydrophobic region including the predicted transmembrane domain and 13 adjacent uncharged residues. Asterisks indicate predicted coiled coil regions with scores above 0.4. Letters above amino acid sequence indicate introduced missense mutations.

FIGS. 2B and 2C show alignments of predicted G1 and G2 motifs (B) and G3 and G4 motifs (C) in Fzo and homologs. Boxes indicate identities with Fzo.

FIG. 2F shows alignment of predicted transmembrane domain and surrounding region in Fzo and homologs. Charged residues are in boldface. Asterisks indicate 13- and 20-residue uncharged regions in Fzo; note similar distribution of charged and uncharged residues in homologs.

FIG. 2G is alpha helical projections of homologous regions near the N termini of Fzo and the *C. elegans* homolog showing hydrophobic, acidic, and basic/polar faces.

FIG. 2H is predicted isoelectric points for regions of Fzo and homologs after conceptual division at the transmembrane region. Gray bars, N terminus to transmembrane region; black bars, transmembrane region to C terminus.

DESCRIPTION OF THE SPECIFIC EMBODIMENTS

Figures 1A, 1B:
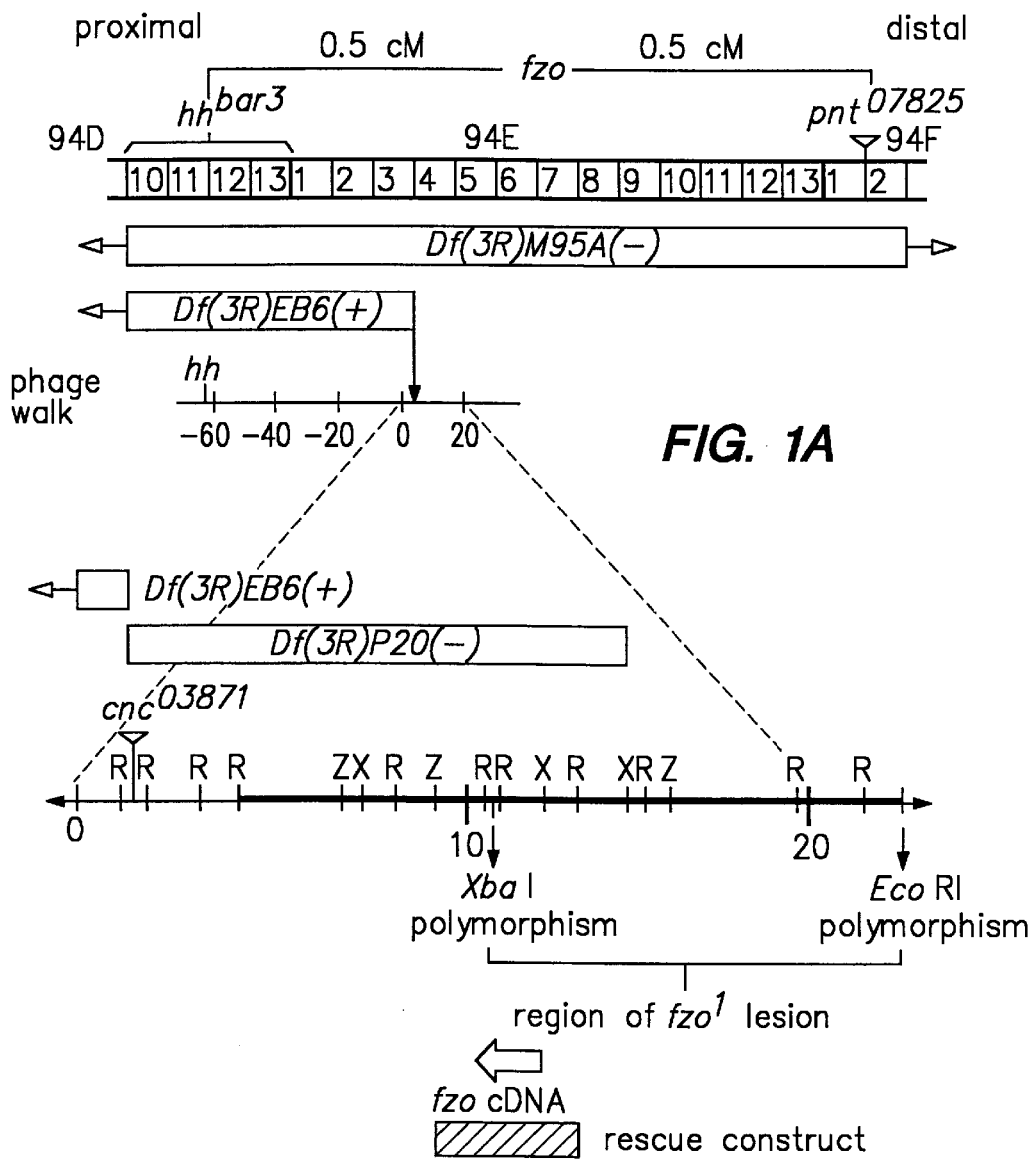
FIG. 1A is a genetic, cytological, and molecular map of the fzo region on chromosome 3R. Stippled numbered boxes represent polytene chromosome bands; open bars are deficiencies, with + indicating complementation of fzo and − indicating failure to complement. The distal breakpoint of Df(3R)EB6 is at +2 kb on a genomic phage walk that extends 90 kb distal from hh.
FIG. 1B is a molecular map of the fzo region of the genomic walk, with coordinates 0 to 20 indicated in kb. Deficiencies represented as in (A). Restriction sites: R, EcoRI; X, XbaI; Z, XhoI. Thick line on molecular map represents genomic DNA used to screen testis cDNA library. This region indicates a genomic fragment that has all sequences required to express fzo in vivo, and to restore fzo function in mutants.

Mitofusin genes and proteins are provided. The mitofusin Fzo is the first known protein mediator of mitochondrial fusion. As used herein, the term "mitofusin" indicates the Drosophila Fzo protein or any of its homologs from insects, other invertebrates, yeast, and vertebrates, including mouse and humans.

The provided mitofusin genes and fragments thereof and genomic regulatory regions are useful in the production of mitofusin protein, as a probe for detection of mitofusin specific sequences and related genes, and for the modulation of gene activity. The encoded mitofusin protein is useful in enhancing the fusion of mitochondria, as an immunogen to raise specific antibodies, in drug screening for compositions that mimic or modulate mitofusin activity or expression, including altered forms of mitofusin protein.

The mitofusin genes and encoded proteins may be used to drive or mediate mitochondrial fusion, for the purposes of introducing intact or partial mitochondrial genomes into mitochondria in diseased host cells or tissues, either in culture or in the intact animal or individual. The use of mitofusin proteins to drive fusion of membrane-bound entities, e.g. mitochondria, in vitro enables investigation of the mechanism of mitochondrial fusion, recombination or complementation between mitochondrial DNA molecules and maintenance of mitochondrial genomes.

Mitofusins are herein identified in *D. melanogaster, S. cerevisiae, C. elegans*, and humans. Specific examples of mitofusin genes are provided in SEQ ID NO:1 (Drosophila) and SEQ ID NO:3 (human). The respective encoded proteins are provided as SEQ ID NO:2 and SEQ ID NO:4, respectively. Two distinct forms have been identified in humans.

The yeast, worm and human homologs share signature conserved features with Drosophila Fzo protein. All are large GTPases with a predicted trans-membrane domain flanked by predicted coiled-coil regions near the C-terminus. The region of the protein C-terminal to the predicted trans-membrane domain has a high pI, characteristic of proteins found in the mitochondrial matrix, while the region of the protein N-terminal to the predicted trans-membrane domain has a lower pI, characteristic of cytoplasmic proteins. These observations, coupled with the association of mitofusin protein with mitochondria at the time of fusion, indicate that mitofusins are inserted into mitochondria with the C-terminal tail in the mitochondrial matrix and the GTPase domain either between the inner and outer mitochondrial membranes or exposed on the cytoplasmic face of mitochondria. The predicted GTPase activity is required for mitochondrial fusion in vivo, but not for import of the protein into or association with mitochondria.

Nucleic Acids encoding Mitofusins

The nucleic acid sequence encoding a mitofusin may be cDNA or genomic DNA or a fragment thereof. The term "mitofusin gene" shall be intended to mean the open reading frame encoding specific mitofusin polypeptides, introns, as well as adjacent 5' and 3' non-coding nucleotide sequences involved in the regulation of expression, up to about 1 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a mitofusin protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

Genomic regions of interest include the non-transcribed sequences 5' or 3' to a mitofusin gene, for example as shown in FIG. 3B. This region of DNA contains the native promoter elements that direct expression of the linked fzo gene. A promoter region will usually have at least about 100 nt of sequence located 5' to a mitofusin gene and will often extend 5' to include other regulatory elements.

The sequence of this 5' region may be utilized for promoter elements, including enhancer binding sites, that provide developmental regulation in tissues where mitofusins are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of mitofusin expression, especially in different tissues or stages of development, and to identify cis acting sequences and trans acting actors that regulate or mediate mitofusin expression. Such transcription or translational control regions may be operably linked to a mitofusin gene in order to promote expression of wild type or altered human or Drosophila mitofusins or other proteins of interest in cultured cells, or in embryonic, fetal or adult tissues, and for gene therapy.

In addition coding sequences may be used to identify cis acting sequences and possible trans-acting factors that regulate or mediate import of mitofusins into or on to mitochondria. Such mitochondrial import signals may be operably linked to a mitofusin or other gene to promote import of wild-type or altered mitofusins or other proteins of interest into or onto mitochondria in vivo or in vitro.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The mitofusin genes are isolated and obtained in substantial purity, generally as other than an intact chromosome. Usually, the DNA will be obtained substantially free of other nucleic acid sequences that do not include a mitofusin sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying mitofusin related genes. Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403–10.

The amino acid sequence similarity between invertebrates and vertebrates is sufficient to identify homologous genes. Regions of more highly conserved sequence are identified through a comparison of the provided sequences, for examples as shown in FIG. 4B and 4C. Such conserved regions are used to design degenerate oligonucleotide primers, as known in the art. Conveniently, the primers are used in an polymerase chain reaction amplification with cDNA or genomic DNA from the target organism as a substrate. The resulting amplified nucleic acid product comprises a fragment of the mitofusin from the target organism, and can be used to isolate the complete gene by various methods known in the art, including rapid amplification of cloned ends (RACE), hybridization to cDNA libraries, etc.

Nucleic acids having sequence similarity are detected by hybridization under low stringency conditions, for example, at 50° C. and 10XSSC (0.9 M saline/0.09 M sodium citrate) and remain bound when subjected to washing at 55° C. in 1XSSC. Sequence identity may be determined by hybridization under stringent conditions, for example, at 50° C. or higher and 0.1XSSC (9 mM saline/0.9 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, Caenhorabditis, etc.

The DNA may also be used to identify expression of the gene in a biological specimen. The manner in which one probes cells for the presence of particular nucleotide sequences, as genomic DNA or RNA, is well established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of mitofusin gene expression in the sample.

The sequence of a mitofusin gene, including flanking promoter regions and coding regions, may be mutated in various ways known in the art to generate targeted changes in promoter strength, sequence of the encoded protein, etc. The DNA sequence or product product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAg system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al, *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989).

Such mutated genes may be used to study structure-function relationships of mitofusins, or to alter properties of the protein that affect its function or regulation. For example, constitutively active fusogens, or a dominant negatively active protein to block fusion, may be created in this manner.

Mitofusin Polypeptides

The subject gene may be employed for producing all or portions of the mitofusin protein. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a mitofusin gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis,*

*S. cerevisiae*, insect cells in combination with baculovirus vectors, or cells of a higher organism such as vertebrates, particularly mammals, e.g. COS 7 cells, may be used as the expression host cells. In many situations, it may be desirable to express the mitofusin gene in eukaryotic cells, where the mitofusin gene will benefit from native folding and post-translational modifications. Small peptides can also be synthesized in the laboratory. Peptides that are subsets of a complete mitofusin sequence, usually at least about 8 amino acids in length, more usually at least about 12 amino may be used to identify and investigate parts of the protein important for function, such as the GTPase domain, mitochondrial import signals, or the coiled-coil regions, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The use of the expressed protein for in vitro models of mitochondrial fusion is of particular interest. The protein may be used to explore conditions and sequences that are required for association of the protein with mitochondria in cell extracts, and for setting up in vitro systems to assay mitochondrial fusion.

The expressed mitofusin polypeptides are used for the production of antibodies, where short fragments provide for antibodies specific for the particular polypeptide, and larger fragments or the entire protein allow for the production of antibodies over the surface of the polypeptide. Antibodies may be raised to the wild-type or variant forms of mitofusin. Antibodies may be raised to isolated peptides corresponding to these domains, or to the native protein, e.g. by immunization with cells expressing mitofusin, immunization with liposomes having mitofusin inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. if desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Diagnostic Uses

Biochemical studies may be performed to determine whether a sequence polymorphism in a mitofusin coding region or control regions is associated with disease, particularly degenerative diseases associated with mitochondrial defects, e.g. amyotrophic lateral sclerosis, Huntington's disease, Parkinson's disease, and Alzheimer's disease. Disease associated polymorphisms may include mutations that alter expression level, that affect the fusogenic activity of the protein, that alter the subcellular localization of the mitofusin, etc.

Changes in the promoter or enhancer sequence that may affect expression levels of mitofusin can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyl transferase, etc. that provides for convenient quantitation; and the like.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express a mitofusin may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of current techniques may be found in Sambrook, et al. *Molecular Cloning: A Laboratory Manual*, CSH Press 1989, pp.14.2–14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine(TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to a wild-type mitofusin sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences. Alternatively, where a polymorphism creates or destroys a recognition site for a restriction endonuclease, the fragment is digested with that endonuclease, and the products size fractionated to determine whether the fragment was digested. Fractionation is performed by gel or capillary electrophoresis, particularly acrylamide or agarose gels.

Hybridization with a polymorphism specific probe may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences.

Screening for mutations in mitofusin may be based on the functional or antigenic characteristics of the protein. Various immunoassays designed to detect polymorphisms in mitofusin proteins may be used in screening. Where many diverse genetic mutations lead to a particular disease phenotype, functional protein assays have proven to be effective screening tools. The activity of the encoded mitofusin protein may be determined by comparison with the wild-type protein.

Antibodies specific for a mitofusin may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal mitofusin in patient cells. For example, detection may utilize staining of cells or histological sections, performed in accordance with conventional methods. Cells are permeabilized to stain intra-mitochondrial and/or cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Determination of the subcellular localization of mitofusin through antibody binding may be used in mutation analysis to detect mutations that cause failure to express or properly localize mitofusin proteins. The assay can be performed by immunohistochemistry or immunofluorescence, where the cell sample is stained with a mitofusin specific antibody followed by labeled secondary antibodies as described above to determine whether mitofusin is properly localized in the mitochondria. Alternatively, cell lysates may be fractionated and the level of mitofusin in the mitochondrial fraction quantitated.

Other diagnostic assays of interest are based on the functional properties of mitofusin proteins. For example, a functional assay may be based on the membrane changes mediated by mitofusin gene products. Other assays may, for example, detect conformational changes, or changes in the subcellular localization of mitofusin proteins.

Modulation of Gene Expression

The mitofusin genes, gene fragments, or the encoded protein or protein fragments are useful in gene therapy to treat degenerative and other disorders involving mitochondria, including myopathies and Alzheimer's disease. Expression vectors may be used to introduce the mitofusin gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or mitofusin protein may be introduced into tissues or host cells by any number of routes, including viral infection, microinjection, or fusion of vesicles or mitochondria. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the mitofusin or DNA, then bombarded into skin cells.

Antisense molecules can be used to down-regulate expression of mitofusin in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'—S—phosphorothioate,3'—S—5'—O—phosphorothioate,3'—CH2-5'—O—phosphonate and 3'—NH—5'—O—phosphoroamidate. Peptide nucleic acids replace the entire ribose phosphodiester backbone % with a peptide linkage. Sugar modifications are also used to enhance stability and affinity. The α-anomer of deoxyribose may be used, where the base is inverted with respect to the natural β-anomer. The 2'—OH of the ribose sugar may be altered to form 2'—O—methyl or 2'—O—allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5- propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridyiCu(II), capable of mediating mRNA hydrolysis are described in Bashkin et al. (1995) *Appl Biochem Biotechnol* 54:43–56.

Cell and Animal Models

The subject nucleic acids can be used to generate genetically modified non-human animals or site specific gene modifications in cell lines, for the study of mitofusin function or regulation, or to create animal models of diseases, including mitochondrial diseases, muscle myopathies, neurodegenerative disorders, and aging. The term "transgenic" is intended to encompass genetically modified animals having a deletion or other knock-out of mitofusin gene activity, having an exogenous mitofusin gene that is stably transmitted in the host cells where the gene may be altered in sequence to produce a modified protein, or having an exogenous mitofusin promoter operably linked to a reporter gene. Transgenic animals may be made through homologous recombination, where the mitofusin locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Investigation of genetic function may also utilize non-mammalian models, particularly using those organisms that are biologically and genetically well-characterized, such as *C. elegans, D. melanogaster* and *S. cerevisiae*. The subject gene sequences may be used to knock-out corresponding gene function or to complement defined genetic lesions in order to determine the physiological and biochemical pathways involved in mitofusin function. Drug screening may be performed in combination with complementation or knock-out studies, e.g. to study progression of degenerative disease, to test therapies, or for drug discovery.

The modified cells or animals are useful in the study of mitofusin function and regulation. For example, a series of small deletions and/or substitutions may be made in the mitofusin gene to determine the role of different domains in GTPase activity, membrane fusion, etc. Specific constructs of interest include, but are not limited to, anti-sense mitofusin constructs to block mitofusin expression, expression of dominant negative mitofusin mutations, and over-expression of a mitofusin gene. One may also provide for expression of the mitofusin gene or variants thereof in cells or tissues where it is not normally expressed or at abnormal times of development. In addition, by providing expression of mitofusin protein in cells in which it is otherwise not normally produced, one can induce changes in mitochondrial behavior.

DNA constructs for homologous recombination will comprise at least a portion of the mitofusin gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting chimeric animals screened for cells bearing the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on mitochondrial fusion, to test potential therapeutics or treatment regimens, etc.

Drug Screening Assays

By providing for the production of large amounts of mitofusin protein, one can identify ligands or substrates that bind to, modulate or mimic the action of mitofusin. Drug screening identifies agents that provide a replacement or enhancement for mitofusin function in affected cells. A wide variety of assays may be used for this purpose, including labeled in vitro protein-protein binding assays, protein-DNA binding assays, protein-mitochondria or protein mitochindria fraction, electrophoretic mobility shift assays, immunoassays for protein binding, and the like. All or a fragment of the purified protein may also be used for determination of three-dimensional crystal structure, which can be used for modeling intermolecular interactions, membrane fusion, etc. Altered mitofusin molecules, either as an isolated recombinant protein, or as a genetically modified cell or animal model may be assayed to investigate structure function parameters, including but not limited to potential mitochondrial import sequences, protein interaction domains, GTPase motifs, and dominant negative acting forms of the protein.

The term "agent" as used herein describes any molecule, e.g. protein or pharmaceutical, with the capability of altering or mimicking the physiological function of a subject mitofusin. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental Procedures

Fly Strains and Culture. Flies were grown on standard cornmeal molasses agar media at 25° C. All visible markers and balancer chromosomes were as described in Flybase (1996) Nucleic Acids Res. 24, 53–56 (flybase.bio.indiana.edu) unless otherwise noted.

The $fzo^1$ allele was isolated in a screen for ethyl methanesulfonate(EMS) induced recessive male sterile mutations. The $fzo^2$ allele was isolated in an EMS screen essentially as described in Lin et al. (1996) Devel. 122:1331–1341, except that mutagenized chromosomes were tested for failure to complement $fzo^1$. One new allele, $fzo^2$, was identified from 1799 mutagenized third chromosomes screened.

The deletions Df(3R)M95A (94D; 95A3) and Df(3R)EB6 (94C2-5; 94E3; Mohler et al. (1995) Devel. 121, 237–247) were gifts from G. Reuter and J. Mohler, respectively. The Df(3R)P2O deletion was generated by mobilizing a lethal $ry^+$ marked P element in 94E3-5 associated with the $cnc^{03871}$ allele as follows. Flies transheterozygous for $cnc^{03781}$ and a TM3, Sb chromosome carrying the Δ2–3 transposase insert (Reuter et al. (1993) Dros. Inf. Serv. 72, 78) were crossed to ry e bar3 tx/TM3, Sb flies. F1 cnc$^{03781*}$/ry e bar3 tx males which had lost the P(ry+) and therefore had ry$^-$ eyes were crossed to e fzo$^1$/TM3, Ser females. F2 cnc$^{03781*}$/e fzo$^1$ males were tested for the fzo phenotype, and stocks of new alleles were recovered by crossing together male and virgin female cnc$^{03781*}$/TM3, SerF2 siblings. From among approximately 200 ry$^-$ chromosomes tested, two deletions failing to complement fzo$^1$ were identified. Molecular breakpoints of the smaller deletion, Df(3R)P2O were mapped by Southern hybridization analysis using standard methods. Df(3R)P2O failed to complement mutations in cnc and was therefore not homozygous viable.

Fertility was determined by placing individual flies in yeasted vials with three males or virgin females as appropriate and scoring the presence or absence of larvae after seven days at 25° C. Progeny of tested females were counted. At least ten individual males and four individual females for each of the allelic combinations fzo$^1$/fzo$^1$, fzo$^1$/fzo$^2$, fzo$^1$/Df(3R)P2O, and fzo$^2$/Df(3R)P2O, as well as heterozygous sibling classes fzo/TM3 or Df(3R)P2O/TM3were tested. (The fzo$^2$chromosome carried a secondary lethal and could not be made homozygous.) The effects of fzo$^1$ and fzo$^2$ mutations on viability were tested by crossing five individual females of each of the above allelic combinations to Df(3R)P2O/TM3 males at 25° C. and comparing numbers of fzo/Df progeny to total progeny. Progeny were collected for nine days after eclosion began.

Light and Electron Microscopy. For light microscopy, testes from the above genotypes as well as from wild type Oregon R flies were dissected in TB1 buffer (7 mM K$_2$HPO$_4$, 7 mM KH$_2$PO$_4$ [pH 6.7], 80 mM KCl, 16 mM NaCl, 5 mM MgCl$_2$, 1% PEG-6000), opened with forceps to allow spillage of contents, placed under cover slips, and examined immediately by phase contrast microscopy with a Zeiss Axiophot microscope. To check for a mitochondrial membrane potential, 10 μg/ml rhodamine 123 was included in the dissection buffer and samples examined under epifluorescence.

For ultrastructural analysis by transmission electron microscopy, testes were dissected in TB1 and immediately placed in fixative (2% glutaraldehyde, 1% paraformaldehyde, 0.1 M sodium phosphate or sodium cacodylate buffer [pH 7]). After overnight fixation, samples were washed in 0.1% phosphate or cacodylate buffer for 15 minutes and stained with 1% osmium tetroxide in the same buffer for two hours. Testes were washed three times in water, stained for 1 hour in 1% uranyl acetate, washed three times in water and dehydrated through an ethanol series (30%, 50%, 70%, 95%, 100%). After five minutes in 1:1 ethanol: propylene oxide and five minutes in propylene oxide, samples were embedded in Spurr's resin and polymerized overnight at 60° C. Thin sections (80–90 nm) were cut with a Reichert-Jung microtome, placed on Formvar-coated slot grids, and examined on a Phillips 410 transmission electron microscope.

Recombination Mapping. For initial meiotic mapping, females heterozygous for an e fzo$^1$ chromosome and a ru h th st p$^p$ cu sr ca chromosome were crossed to ru h th st p$^p$ cu sr Bsb/TM3 or ru h th st cu e Pri ca/TM3 males. Male progeny with markers indicating single recombination events were selected for each interval and individually crossed to three e fzo$^1$/TM3 females to score fzo and make stocks of the recombinant chromosomes with TM3. The fzo$^1$ mutation mapped between e and ca, roughly 9 cM distal to e.

To localize fzo$^1$ further, p$^p$ e fzo$^1$/hh$^{bar3}$ tx females were crossed to e hh$^{bar3}$ tx/TM3 males and recombinant male progeny crossed individually to e fzo$^1$/TM3 females to score fzo and make stocks with TM3. fzo$^1$ mapped 0.58±0.17 cM distal to hh$^{bar3}$ (FIG. 4), based on 227 recombinants between hh$^{bar3}$ and tx.

RFLP Mapping. The fzo$^1$ mutation was further localized by recombination with respect to restriction fragment length polymorphisms (RFLPs) in the interval between hh$^{bar3}$ and a ry$^+$ marked P element insertion in the pointed gene associated with the pnt$^{07825}$ allele. Briefly, females transheterozygous for ry$^{506}$ hh$^{bar3}$ fzo$^1$ (parental chromosome 1) and ry$^{506}$ pnt$^{07825}$ (parental chromosome 2) were crossed to ry$^{506}$ e hh$^{bar3}$; tx/TM3 males. Recombinant F1 Sb$^+$ progeny that were phenotypically either hh$^{bar-}$ ry$^+$ or hh$^{bar3+}$ ry appeared at a frequency of 31 per 2995 flies, indicating that hh$^{bar3}$ and pnt$^{07825}$ were 1.04+/−0.18 cM apart. Males representing each of these two reciprocal recombinant classes were crossed individually to e fzo$^1$/TM3 females to score fzo on the recombinant chromosomes and to construct stocks with TM3. The fzo$^1$ mutation mapped in the center of the interval, 0.5 cM distal to hh$^{bar3}$ and 0.5 cM proximal to pnt$^{07825}$.

RFLPs between the two parental chromosomes were identified using Southern blot analysis. Standard molecular biology techniques were used throughout this work, and DNA fragments were purified with a QIAquick kit (QIAGEN) as per the manufacturer's instructions. Genomic DNA was isolated from flies homozygous for parental chromosome 1 as well as from flies transheterozygous for parental chromosomes 1 and 2 (the P element insertion on parental chromosome 2 was a recessive lethal). The parental genomic DNAs were digested separately with 34 standard four-, five-, and six-cutter restriction enzymes, electrophoresed, blotted, and hybridized with several different radiolabeled DNA fragments from the distal third of a 90 kb genomic walk (Mohler et at. (1991) Mech. Devel. 34, 3–10). At least one RFLP between the two parental chromosomes was detected for each probe. Genomic DNA was isolated from 35 recombinant stocks (either from homozygotes or from flies transheterozygous for the recombinant chromosome and parental chromosome 1). These DNAs were digested with the restriction enzymes previously shown to have polymorphic sites in the region, blotted, and probed with the appropriate fragments. Analysis of linkage between these molecular markers and fzo$^1$ defined the region of the fzo$^1$ mutation to be between a polymorphic XbaI site at +11 and a polymorphic EcoRI site at +22 on the genomic walk (Mohler et al., 1991). The XbaI and EcoRI RFLPs segregated from fzo$^1$ in one and two of the 35 recombinants, respectively.

Isolation of cDNAs and Sequence Analysis. Radiolabeled EcoRI restriction fragments corresponding to +5 to +22 on the genomic walk, were used to probe a λ-ZAP (Stratagene) testis cDNA library. Eighteen positive cDNA clones of various lengths were shown by Southern hybridization analysis to be from the same transcription unit. The seven longest cDNAs were 2.4 kb and had identical restriction maps. One of these was mapped to genomic DNA by Southern hybridization and, consistent with restriction mapping analysis, seemed to have no detectable introns. This cDNA was sequenced on both strands by the dideoxy chain termination method using the ABI PRISM dye terminator cycle sequencing system (Perkin-Elmer). T3 or T7 primers were used on the intact CDNA or dropout subclones, and 19- or 20-mer oligonucleotides were synthesized to prime sequencing runs through any remaining gaps. Representative members of each shorter cDNA class were restriction mapped, partially sequenced, and shown to be truncated versions of the longer class.

The cDNA (2399 bp) was conceptually translated with DNA Strider software and the Fzo predicted protein sequence compared using the BLAST program to nucleotide sequences in GenBank and dbEST translated in all reading frames. Significant homology was detected to predicted proteins from H. sapiens, M. musculus, C. elegans, and S. cerevisiae. The human cDNA clone from which a human fetal brain EST (GenBank T06373) was derived was obtained from American Type Culture Collection and sequenced on one strand. Predicted proteins encoded by Fzo homologs were themselves subjected to homology searches as above. Alignments were done with the help of the CLUSTALW program using DNAstar software.

Analysis of the Fzo predicted protein with the BLOCKS program indicated similarity to the dynamin family in the vicinity of the P-loop, a motif found in nucleotide-binding proteins and designated as the G1 GTPase motif (Bourne et al., (1991) Nature 349, 117–127). The sequences of Fzo and homologs were analyzed for predicted transmembrane domains and regions likely to form coiled coils with the TMpredict program and the COILS program, respectively. The Compute pI/Mw program on the ExPASy Molecular Biology Server was used to calculate predicted isoelectric points.

P element Mediated Germline Transformation. A 3 kb genomic fragment was isolated from an XhoI/XbaI digestion of phage D14 DNA (which corresponds to +3 to +16 on the genomic walk) and subcloned into the $w^+$-marked P element transformation vector pCaSpeR4 (Thummel and Pirrotta (1992) Dros. Inf. Serv. 71, 150) to make plasmid pKH2. The 2.4 kb EcoRI restriction fragment from phage D14 had previously been subcloned into pUC9 to make construct D5-19; a 1 kb XbaI/EcoRI fragment was isolated from a digestion of D5-19 and subcloned into pKH2 to make pKH3fzo$^+$. The resulting 4 kb insert in the pKH3fzo$^+$ rescue construct contained the genomic region of the full length fzo cDNA plus approximately 1 kb 5' and 500 base pairs 3'.

The pKH3fzo$^+$ plasmid and a plasmid encoding the $\Delta 2$–3 constitutively active transposase were mixed in a 3:1 molar ratio to a final DNA concentration of 0.4 mg/ml and injected into y $w^{67}$ or $w^{1118}$ embryos. Three independent fzo$^+$ insertions, one on the second chromosome and two on the third, were isolated from the progeny of 32 fertile injectees. An additional insertion on the second chromosome was obtained by mobilizing one of the third chromosome insertions with the TM3, Sb $\Delta 2$–3 transposase source. To test for rescue, all four independent fzo$^+$insertions were crossed into w; fzo mutant backgrounds by independent assortment for the second chromosome insertions and by recombination onto a hh$^{bar3}$ fzo$^1$ chromosome and then independent assortment for the third chromosome insertions, which were tested for rescue only of allelic combinations with fzo$^1$.

Site-directed Oligomutagenesis and Retransformation with Mutated fzo Transgenes. To introduce mutations into the Fzo predicted GTP-binding domain, a 1.8 kb Xba I/BamHI restriction fragment (representing the first two thirds of the fzo coding region) from the pKH3fzo$^+$ germline transformation construct (see above) was subcloned into Bluescript SK-. Using standard methods, mutagenesis was performed with oligonucleotides of the sequences [SEQ ID NO:5] 5' ACCTCAAATGGAACTAGTGCCGTGATC 3' and [SEQ ID NO:6] 5' TACTCMCAATCTATGGGATMG3'. The former exchanged AA for CT at nucleotides corresponding to those at positions 369–370 in the fzo cDNA, introducing a SpeI restriction site and changing the encoded amino acid at position 99 from a lysine to a threonine. The latter replaced a G with a T at nucleotide 819, eliminating a ClaI restriction site and changing the encoded amino acid at position 249 from an arginine to a leucine. Mutagenized constructs were selected by virtue of the above mentioned altered restriction sites. For each mutagenized construct, a 1.8 kb Xba I/BamHI restriction fragment was subcloned back into the 10 kb Xba I/BamHI vector fragment from plasmid pKH3fzo$^+$ to create two new germline transformation constructs, pKH$_3$fzo$^{K99T}$ and pKH3fzo$^{R249L}$, which were injected into fly embryos as described above. For both these constructs, the XbaI and BamHI restriction sites used for the final subcloning were regenerated by the ligations. In addition, the reading frame remained unchanged at the mutagenesis and subcloning sites, as shown by detection of mutant proteins with anti-Fzo$^{605-718}$ antibodies, which recognize only epitopes encoded by regions 3' to the sites of ligation and mutagenesis.

To test for rescue of the mutant phenotype by the fzo$^{K99T}$ and fzo$^{R249L}$ mutant transgenes, respectively, appropriate crosses were made to introduce separately the eight and five independent second chromosome transgene insertions into fzo mutant backgrounds. To test for any dominant effect, appropriate crosses were made to obtain males with one wild type copy of fzo and as many as four (fzo$^{K99T}$) or six (fzo$^{R249L}$) different copies of the mutated transgenes.

RNA in situ Hybrdization. For in situ hybridization to testes, digoxygenin-labeled RNA probes representing both the fzo cDNA sense and anti-sense strands (primed with T7 or T3 primers on a linearized cDNA construct) were made and submitted to alkaline hydrolysis (1 hour) as described in the Genius 4 RNA Labeling Kit user's guide (Boehringer Mannheim). Paraformaldehyde fixation of freshly dissected testes was as in Tautz (1989) Chromosoma 98, 81–85 except no heptane or methanol was used. Subsequent treatment was as in Gonzalez (1994) Techniques for studying mitosis in Drosophila. In The cell cycle: A practical approach, R. Brookes and P. Fantes, eds.: IRL, Oxford University Press), pp. 143–175, except 50 µg/ml heparin was included in the hybridization solution (HS); hybridization and early washes were at 65° C., and the secondary antibody was preadsorbed to Drosophila embryos and diluted 1:2000. Mounted preparations were examined under Nomarski optics with a Zeiss Axiophot microscope.

Generation of anti-Fzo antibodies. Antibodies were raised to a fusion protein containing a 6-histidine tag and the C-terminal 115 amino acids of Fzo. To make the expression construct, a 0.5 kb BamHI/HindIII restriction fragment from fzo cDNA1 (the HindIII site is from the Bluescript SK-multiple cloning site) was subcloned into vector pQE30 (QIAGEN). The fusion protein was induced, harvested under denaturing conditions, and purified on a Ni-NTA column with imidazole elution as described in the QIAexpressionist manual (QIAGEN). Aliquots from each column fraction were electrophoresed on an SDS-polyacrylamide gel and stained with Coomassie Blue. Fractions with greatest purity and highest concentration of the fusion protein were dialyzed in 1.5 M urea, 0.1 M Na phosphate, 0.01 M Tris-HCl, and 500 mM NaCl, pH 7. The fusion protein formed a precipitate at urea concentrations below 4 M. After dialysis, precipitated protein was emulsified in complete Freund's adjuvant and injected into rabbits; standard schedules were followed for booster injections and serum collections (Berkeley Antibody Company, Richmond Calif.). Approximately 500 mg and 250 mg of the fusion protein were used for initial and booster injections, respectively.

Western Blots. Protein extracts were electrophoresed in 10% SDS-polyacrylamide gels and transferred to nitrocellulose filters in methanol buffer using standard methods.

Testis extracts were prepared by placing freshly dissected testes into a solution containing 8M urea, 0.1M sodium phosphate, and 0.01M Tris-Cl, pH 7 and mixing thoroughly until all proteins had dissolved. One volume of SDS-PAGE sample buffer was added, and the samples were then boiled for 15 minutes and spun at top speed in a microcentrifuge for ten minutes. Eight testes' worth of extract supernatant was loaded in each lane. Whole fly extracts were prepared by homogenizing flies in the above urea solution, with further treatment as above. One fifth of a fly's worth of extract was loaded per lane.

Filters were blocked in Blotto with 0.1% Tween 20 and incubated for two hours at room temperature in either preimmune or anti-Fzo$^{604-718}$ serum (fourth bleed) diluted 1:1200, or mouse monoclonal anti-actin antibody (Amersham) diluted 1:100, in the blocking solution. Subsequent washes, incubation with horseradish peroxidase-conjugated secondary antibodies, and detection were performed as described in the ECL Western Blotting manual (Amersham). The secondary antibodies were diluted 1:7000 (anti-rabbit IgG) or 1:2000 (anti-mouse IgG).

Immunofluorescence. Fly testes were prepared for immunofluorescence staining as described in Hime (1996) J. Cell Sci. 109, 2779–2788. The resulting slides were incubated overnight at 4° C. in preimmune or anti-Fzo$^{604-718}$ serum (fourth bleed) diluted 1:150 in PBTB (phosphate-buffered saline with 0.1% Triton X-100 and 3% bovine serum albumin), washed four times at room temperature in PBTB, and incubated for one hour at 37° C. in FITC-conjugated anti-rabbit IgG (Jackson Labs) diluted 1:200 in PBTB (0.5 mg/ml RNAse was included for samples to be later stained with propidium iodide). Slides were washed 4×10 minutes in PBTB and mounted in 85% glycerol, 2.5% N-propyl gallate. For some samples, 1 μg/ml DAPI (Sigma) was included in the second PBTB wash after incubation in secondary antibody; for others, 1 pg/ml propidium iodide was included in the mounting medium. Samples were examined using epifluorescence on a Zeiss Axiophot microscope; images were collected with a Photometrics cooled CCD camera (courtesy of Bruce Baker). Emissions from different fluorochromes on the same sample were collected separately and overlaid using Adobe Photoshop.

Wild type function of fzo is required for developmentally regulated fusion of mitochondria during Drosophila spermatogenesis. Mutations in fzo cause male sterility associated with defects in mitochondrial fusion during Nebenkern formation in post-meiotic early round spermatids. In wild type testes, mitochondria in each haploid spermatid aggregate beside the nucleus and fuse into a Nebenkern, a phase-dark spherical structure consisting of two inter-wrapped mitochondrial derivatives as viewed by TEM. In fzo mutant males, mitochondria aggregate in early haploid spermatids, forming somewhat misshapen Nebenkerns as viewed by phase contrast microscopy, but fail to fuse into two giant mitochondria. Instead, many smaller mitochondria appear to wrap around each other at the onion stage as viewed by TEM. Despite the prior defects in fusion, mitochondria unfurl and elongate in fzo mutants. At the early elongation stage, unfurling mitochondria in fzo mutants appear fragmented compared to wild type as seen by phase contrast microscopy. At the late elongation stage, two elongating mitochondrial derivatives per spermatid are seen in wild type. In contrast, many elongating mitochondria are associated with each haploid nucleus in fzo. Cross sections through wild type elongating spermatids viewed by TEM reveal two mitochondrial derivatives associated with each axoneme; the major derivative contains electron dense paracrystalline material while the minor does not. Each axoneme in fzo mutant males is associated with a large number of mitochondrial derivatives, with roughly half containing the paracrystalline material characteristic of major derivatives. Thus the defects in fzo mutant spermatids appear specific for mitochondrial fusion, as mitochondrial aggregation, membrane wrapping, and elongation all occur (although the unfused mitochondria do not elongate the full axonemal length because they lack sufficient membrane material). In addition, spermatid mitochondria in fzo mutants take up the dye rhodamine 123 in amounts similar to wild type, indicating presence of a membrane potential and suggesting that fzo mutations probably do not grossly affect respiration.

Figure 2E:
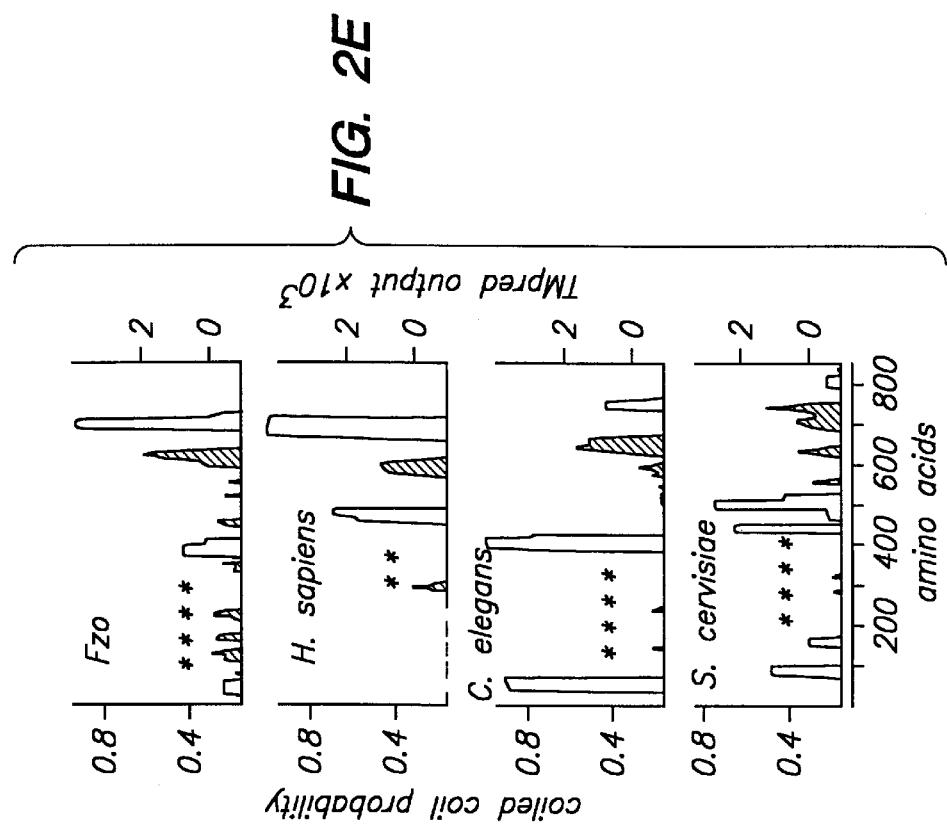
FIG. 2E shows overlaid plots of coiled coil probabilities (open) and hydrophobicity (filled-in) for Fzo and homologs. Sequences were analyzed with the COILS program (MDITK matrix, weighted second and fifth heptad positions) and with the TMpred program using default parameters; a TMpred output of $0.5 \times 10^3$ or above is considered significant. Stars represent GTPase motifs.
Figure 2D:
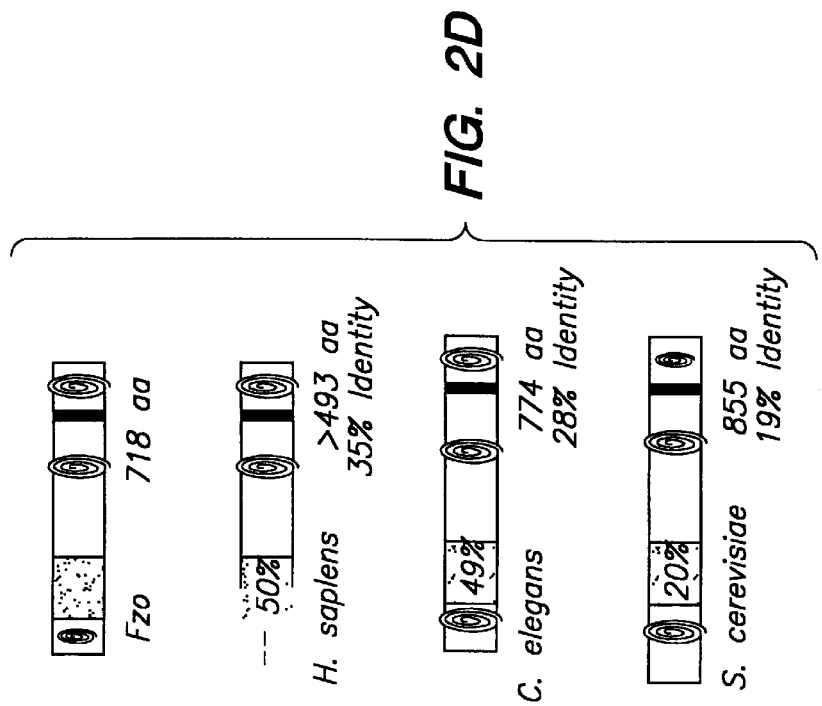
FIG. 2D is a schematic diagram of Fzo and human, *C. elegans*, and *S. cerevisiae* homologs, showing predicted GTPase domain (stippled box) and predicted transmembrane domain (dark bar). Spirals indicate predicted coiled coil regions with probabilities between 0.4 and 1.0 (large spirals) and between 0.2 and 0.4 (small spirals), respectively. Percentage identities to Fzo overall and within the predicted GTPase domains are indicated.

Two EMS-induced alleles, fzo$^1$ and fzo$^2$, were characterized as described above. fzo$^1$/fzo$^1$, fzo$^1$/fzo$^2$, fzo$^1$/Df(3R)P2O, and fzo$^2$/Df(3R)P2O flies showed identical phenotypes, suggesting that both mutations are strong loss of function alleles. The severity of the phenotype was consistent among all spermatids in all testes observed. The fzo$^1$ and fzo$^2$ mutations did not noticeably affect female fertility or overall viability of the animal.

fzo encodes a novel conserved predicted transmembrane GTPase. The fzo$^1$ mutation was mapped by recombination to 0.5 cM distal of hh$^{bar3}$ and 0.5 cM proximal of pnt$^{07825}$, in agreement with complementation of fzo$^1$ by Df(3R)EB6 but not by Df(3R)M95A (FIG. 3A). The fzo$^1$ mutation was further localized by RFLP mapping to an 11 kb region defined by polymorphic XbaI and EcoRI sites on an existing genomic phage walk (FIGS. 2A, B). In addition, a 12 kb deficiency (Df(3R)P2O) generated by imprecise excision of a nearby P element (cnc$^{03871}$) failed to complement fzo mutations, consistent with the RFLP mapping data.

cDNA clones corresponding to transcripts from the fzo region were isolated from a testis cDNA library. All eighteen positive clones from the region represented the same transcription unit, based on Southern blot hybridization. The largest cDNA clones were 2.4 kilobases (kb) long and had identical restriction maps. One of these was chosen for further analysis and mapped by Southern blot hybridization to cloned genomic DNA in the fzo region.

To confirm that this transcription unit corresponded to fzo, we introduced a 4 kb genomic fragment containing the candidate locus plus 1 kb of sequence upstream and approximately 500 bp of sequence downstream of the cDNA into flies by P element mediated germline transformation. A single copy of any of four independent transgene insertions fully restored fertility and normal mitochondrial morphogenesis to fzo$^1$/fzo$^1$, fzo$^1$/Df(3R)P2O, and fzo$^1$/fzo$^2$ males (and also fzo$^2$/Df(3R)P2O males, for the second chromosome insertions).

The representative fzo cDNA was sequenced fully on both strands and shown to have a complete open reading frame (ORF) with flanking AT-rich sequences and a single consensus translational start site. The fzo transcription unit encodes a predicted protein of 718 amino acids. Database searches with the amino acid sequence identified ORFs that encode related predicted proteins in mammals, C. elegans, and S. cerevisiae. Human expressed sequence tags (ESTs) from brain (T06373, R20140, T37724), heart (AA248162, AA248083), fibroblasts (W49736), liver/spleen (H58349, AA010217), and pancreas (AA55601) encode predicted peptides homologous to Fzo. The cDNA clone from which a human fetal brain EST (T06373) was derived was sequenced and shown to encode an incomplete predicted protein (lacking its N terminus) with 35% identity to Fzo. The heart, fibroblast, and other brain ESTs are virtually identical to regions of this cDNA, while one of the liver/spleen clones (H58349) and the pancreas EST (Ml 55601) seem to originate from a different gene and encode a 125 residue peptide 56% identical to the C terminus of the human fetal brain gene product. The two human isoforms are both 28% identical to Fzo in this C-terminal region. Four mouse ESTs (W41601, AA99015, AA212845, AA052806) together encode 211 amino acids with 22% identity to the Fzo C terminus and 84% identity to the analogous region in the sequenced human brain homolog. ORFs from C. elegans (U29244, ORF 14) and S. cerevisiae (Z36048) encode complete predicted proteins with 28% and 19% identity to Fzo, respectively (FIGS. 4B–D). The S. cerevisiae predicted protein is itself 24% identical to a partial predicted protein from the thermophilic bacterium Caldocellum saccharolyticum (Li 8965 ORF 6), which is 11% identical to Fzo.

The region of highest homology between the Fzo, human fetal brain (50% identity to Fzo), C. elegans (49%), and S. cerevisiae (20%) predicted proteins is a 186 amino acid region containing four completely conserved signature motifs found in virtually all GTPases (G1–G4 in FIGS. 2A–C). The C. saccharolyticum predicted protein also contains these motifs. Outside the individual motifs there is no significant similarity to any known GTPase. However, the spacing between the GTPase motifs, their N-terminal placement in Fzo and homologs, and the overall predicted protein size are reminiscent of the dynamin family (Warnock and Schmid, 1996 BioEssays 18, 885–893). The G2 motif (Bourne et al., 1991 Nature 349, 117–127) consists only of a conserved threonine and has not been defined in dynamins. Both the Fzo and dynamin families have a conserved threonine exactly 20 residues beyond the G1 motif that we propose represents G2.

Outside the GTPase domain, Fzo and its homologs have moderate homology at the amino acid level (30%, 21%, and 19% identity beween Fzo and the human fetal brain, C. elegans, and S. cerevisiae homologs, respectively) and share several predicted structural features. All have a predicted transmembrane domain near the C terminus embedded in a large (~35 amino acids) uncharged region interrupted by one to three basic residues. All the homologs have predicted coiled coil regions flanking the predicted transmembrane domain, though the C terminal coiled coil probability in the S. cerevisiae homolog is lower than in other homologs. The C. elegans and S. cerevisiae homologs have strongly predicted coiled coil regions near their N termini. The analogous region in Fzo has a lower coiled coil probability (0.23) but is strikingly similar to the C. elegans homolog in its a helical projection, showing clear acidic, hydrophobic, and basic/polar faces. All four homologs are acidic overall between the N terminus and the transmembrane domain, with predicted isoelectric points (pI) near 5, and are basic in the C terminal tail, with predicted pIs near 9 (FIG. 4H). fzo mRNA is expressed in primary spermatocytes. The fzo message was highly expressed in pre-meiotic primary spermatocytes during their growth period but was not detectable at earlier stages in germline stem cells or mitotically dividing spermatogonia. The transcript persisted in meiotic cells but was not detectable in differentiating spermatids. The transcript was present in both $fzo^1/fzo^1$ and $fzo^2/Df(3R)P2O$ testes. A control sense-strand fzo RNA probe did not hybridize in cells of any stage.

Anti-$Fzo^{604-718}$ antibodies detect greatly reduced levels of Fzo in $fzo^1$ and $fzo^2$ mutant testes. Antibodies raised against a fusion protein containing the C-terminal 115 residues of Fzo detected a wide doublet in Western blots of wild type testis extracts. The Fzo protein was partially resistant to extraction and denaturation and under standard denaturing conditions ran predominantly in streaky globs at an apparent molecular weight of 67 kD. When subjected to additional boiling and denaturants, some of the protein shifted up to a smoother band at an apparent molecular weight of 82 kD, the predicted size for Fzo. The wide Fzo doublet was greatly reduced in $fzo^1$ and $fzo^2/Df(3R)P2O$ mutant testes and increased in testes from wild type flies carrying six copies of the $fzo^+$ transgene.

Very low levels of Fzo or a cross-reacting protein with the same mobility pattern were apparent in extracts from whole adult agametic males, indicating expression in somatic tissues. Similar low levels of this protein were seen in agametic females, ovaries, and embryos of all stages and were unaffected in $fzo^2/Df(3R)P2O$ whole male extracts. However, in $fzo^1/fzo^1$ males, the Fzo protein is highly expressed in somatic tissues despite its downregulation in $fzo^1/fzo^1$ testes. The $fzo^1$ mutation therefore appears to affect tissue specific expression of Fzo. Extracts from whole wild type males carrying six copies of the $fzo^+$ transgene showed more Fzo protein than agametic males but considerably less than $fzo^1/fzo^1$ males. Fzo may normally be expressed weakly in somatic tissues; it is therefore possible that Fzo is required elsewhere in addition to the testis and that the $fzo^1$ and $fzo^2$ alleles cause loss of function in the male germline only. Alternatively, the weakly-expressed somatic protein could be a Fzo isoform or an unrelated cross-reacting protein.

The Fzo protein is associated with mitochondria in early spermatids during a short time period that spans mitochondrial fusion. The anti-$Fzo^{604-718}$ antiserum stained onion stage Nebenkerns brightly in wild type spermatids but was undetectable or present at greatly reduced levels in $fzo^1/fzo^1$ or $fzo^2/Df(3R)P2O$ testes, respectively. A wild type fzo transgene in a $fzo^1/fzo^1$ mutant background restored detectable Fzo protein to the Nebenkern.

The Fzo protein was associated with mitochondria in wild type spermatids during a narrow developmental window corresponding to the time that Fzo function is required. Mitochondria align on the spindle equator throughout meiotic divisions; however, the Fzo protein was not detected associated with mitochondria until the end of meiosis, during telophase II. In post-meiotic haploid spermatids, Fzo was associated with aggregating mitochondria and was detected at highest levels associated with onion stage Nebenkerns. The Fzo protein was detected at lower levels associated with early elongation-stage mitochondrial derivatives and was not detected associated with more elongated mitochondria. In testes from flies carrying multiple different copies of the $fzo^+$transgene, the anti-Fzo antibody stained mitochondria much more brightly but with a similar time course to wild type. Preimmune serum did not stain wild type testes.

Conserved residues in the GTPase domain are required for Fzo function but not for targeting of the protein to mitochondria. Mediation of mitochondrial fusion by Fzo appears to require the predicted GTPase activity. Missense mutations in the fzo transgene that alter conserved residues (lysine-99 and arginine-249) required in other GTPases for guanine nucleotide binding were introduced into the fzo transgene construct. For the $fzo^{K99T}$ and $fzo^{R249L}$ transgenes, respectively, none of the eight and five independent insertions on the second chromosome (in one copy or two, for those that were viable as homozygotes) was able to restore fertility or sperm motility to $fzo^1/fzo^1$, $fzo^1/Df(3R)$ P2O, or $fzo^2/Df(3R)P2O$ mutant males. In two copies, the $fzo^{K99T}$ transgene did not detectably improve the subcellular mutant phenotype, while the $fzo^{R249L}$ transgene appeared to allow some mitochondrial fusion. In a wild type background, neither mutant transgene impaired fertility or mitochondrial fusion. $Fzo^{K99T}$ and $Fzo^{R249L}$ mutant proteins were properly localized to spermatid mitochondria with wild type timing of appearance and disappearance.

Fzo is a novel predicted GTPase. The Drosophila fzo gene encodes a conserved predicted GTPase required for mitochondrial fusion during spermatogenesis and associated with mitochondria only during a short time spanning the fusion event. Fzo contains four motifs common to virtually all known GTPases and conserved among Fzo homologs from mammals to yeast. Fzo is the first protein to be assigned a function in this new family of large predicted transmembrane GTPases. Within this family, the GTPase domain placement, motif spacing, and protein size (but not overall sequence) suggest a possible distant relationship with dynamins, which play a central biomechanical role in endocytic membrane trafficking.

Mutations predicted by analogy to diminish guanine nucleotide binding did not affect localization of Fzo to mitochondria but eliminated or reduced its ability to mediate mitochondrial fusion. The $fzo^{K99T}$ mutation, predicted to disallow key hydrogen bonds with the GTP $\beta$ and $\gamma$ phosphates, caused a severe loss of function phenotype. In contrast, the $fzo^{R249L}$ mutation appeared to allow some mitochondrial fusion to occur, though not enough to restore normal sperm morphology or motility. The Fzo arginine-249 is part of the G4 motif and is predicted to contact the ribose moiety of GTP. Nearly all known GTPases have a lysine at positions analogous to $Fzo^{R249}$; perhaps the conservative change to arginine in Fzo and its higher eukaryotic homologs reflects somewhat decreased importance of this residue for stable nucleotide binding. Mutations analogous to $fzo^{R249L}$ in H-ras reduce but do not eliminate GTP binding. It is possible that $Fzo^{R249L}$ may have residual GTP affinity, explaining its partial function.

The $fzo^{K99T}$ and $fzo^{R249L}$ mutations are recessive. Analogous mutations in mammalian dynamins cause dominant negative phenotypes when expressed in tissue culture cells; formation of macromolecular dynamin ring-shaped complexes appears to require GTP binding by all subunits. In contrast to dynamins, Fzo molecules may act individually or form complexes in which only some subunits must bind GTP for proper assembly or function.

Models for mitofusin orientation and function. The conserved overall charge distribution and predicted transmembrane domain of mitofusins are consistent with a possible $N_{out}$-$C_{in}$ orientation on mitochondria. Typically, mitochondrial matrix proteins are more basic (with a higher predicted isoelectric point (pI)) than their cytoplasmic isoforms; similarly, inner mitochondrial membrane proteins are generally basic in the matrix-residing region and more acidic in outside regions. Mitofusins, when conceptually divided at their transmembrane domains, have N termini with predicted pIs of 5.3 to 6 and C termini with pIs of 8.1 to 9.3, suggesting that the C terminus may reside in the matrix.

The Fzo protein has eight acidic residues and only one arginine in its first 50 amino acids, making import via a traditional N terminal targeting signal unlikely. It is possible that the serine-rich nature of this region allows mitochondrial targeting despite the acidic residues. Alternatively, Fzo could be targeted to mitochondria by an internal basic region just C terminal to the predicted transmembrane domain (e.g. residues 621–636), leading to an $N_{out}$-$C_{in}$ orientation, as for the S. cerevisiae Bcs 1 p protein.

The predicted transmembrane region of the Fzo protein consists of 13- and 20-residue uncharged regions separated by an arginine; the organization of hydrophobic and charged residues in this region is structurally conserved among Fzo homologs. This region could potentially span one membrane twice. Alternatively, as overall charge distribution in the protein suggests compartmental separation of the N and C terminal portions, it is plausible although unprecedented that Fzo could span both the inner and outer mitochondrial membranes at a contact site between these two membranes. With the 20-residue region in the inner membrane and the arginine (perhaps with adjacent residues) in the intermembrane space, the 13-residue hydrophobic region could traverse the outer membrane in a $\beta$ sheet conformation, which requires fewer hydrophobic residues to span the membrane than an $\alpha$ helix. This putative $\beta$ sheet region could form lateral hydrogen bonds with other copies of itself or with $\beta$ sheet transmembrane regions from other outer membrane proteins like porin. In mammalian tissue culture cells, mitochondrial fusion appears to initiate where inner/outer membrane contact sites on each of two separate mitochondria are apposed. Stable inner/outer membrane contact sites that are independent of protein import channels have been observed; perhaps the primary function of these sites is for mitochondrial fusion. Mitofusins are good candidates to act at such putative fusion-mediating contact sites between inner and outer mitochondrial membranes.

If mitofusins span both membranes with its C terminus in the matrix, then the predicted GTPase domain would be oriented toward the cytoplasm, where it could mediate interactions between mitochondria or regulate assembly of additional proteins. The mitofusin protein could act as part of a ligand/receptor pair between separate mitochondria, binding to copies of itself or to other molecules displayed on the outer mitochondrial membrane. Alternatively, the mitofusin protein could recruit other molecules to form a complex that links adjacent mitochondria. Several regions of mitofusin could potentially participate in such protein-protein interactions, including the predicted coiled coil region at residues 377–400 as well as the N-terminal serine-rich region with its adjacent predicted "tri-amphipathic" $\alpha$ helix.

In either case, GTP binding and hydrolysis by mitofusins may regulate the specificity of these protein-protein interactions, as Rab GTPases seem to regulate formation of the SNARE complex prior to membrane fusion in the secretory and endocytic pathways. Alternatively, the mitofusin predicted GTPase may have a biomechanical role, as may dynamin GTPases in the formation of endocytic vesicles. GTP hydrolysis could cause a conformational change in the mitofusin itself or in other recruited proteins, bringing membranes close together and/or exposing residues that could act as a hydrophobic bridge between the fusing mitochondria. Candidate regions in mitofusin to serve as such a bridge would be the hydrophobic faces of either the tri-amphipathic $\alpha$ helix or the other predicted coiled coil regions. This scenario would be analogous to influenza virus fusion, during which low pH triggers a conformational change in HA, or to a proposed conformational change in SNARE proteins that may be induced either by NSF ATP hydrolysis or by a yet unidentified GTPase during secretory membrane fusion events.

The orientation of the mitofusin protein may be different from that postulated in the above model, inserting in only one of the two mitochondrial membranes and/or taking on an $N_{out}$-$C_{in}$ conformation. It is possible that the transmembrane region traverses one membrane twice (or loops partially into a membrane from one side), causing both ends of the mitofusin to be in the same compartment. mitofusins could mediate fusion of only one membrane, with other fusogens acting on the other. Alternatively, the mitofusin protein may be only indirectly required for fusion, playing a role in modification or mitochondrial import of the molecules that participate directly.

The Mitofusin family of predicted GTPases. The mammalian mitofusins may mediate mitochondrial fusion and/or other functions in diverse cell types. ESTs from genes encoding the human homologs were derived from brain, heart, pancreas, liver/spleen, and fibroblast cDNA libraries. Mitochondrial fusion is known to occur in liver and is suggested to occur in certain rat neuronal cells and mouse 3T6 fibroblasts. Mammalian spermatid mitochondria do not undergo massive fusion but become connected in a helical sheath around the sperm midpiece. End-to-end contacts between mitochondria in this sheath contain structurally distinct "stud-like bridging elements", which seem to allow transmission of membrane potential through the helix. Formation of these connections, which are also seen in rat cardiac tissue, may require the same. protein mediators that are needed for full mitochondrial fusion in other cells. Analysis of the role of mitofusins in diverse organisms will allow assignment of a general function for this new family of large multidomain GTPases, for which the name "mitofusins" is proposed.

GenBank Accession Numbers

The GenBank accession number for the fzo cDNA is U95821 and for the partial cDNA encoding the fzo human fetal brain homolog is U95822.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A purified polypeptide composition comprising at least 50% by weight of the protein present as a mitofusin protein.

2. A purified polypeptide according to claim 1, wherein said polypeptide comprises the amino acid sequence set forth in SEQ ID NO:2.

3. A purified polypeptide according to claim 1, wherein said polypeptide comprises the amino acid sequence set forth in SEQ ID NO:4.

4. A purified polypeptide fragment of at least 2 amino acids, and comprising a contiguous sequence set forth in one of SEQ ID NO:2 or SEQ ID NO:4.

5. A purified mitofusin polypeptide encoded by a nucleic acid that hybridizes under stringent conditions to the complementary sequence to SEQ ID NO:1.

6. The mitofusin polypeptide of claim 5, wherein said polypeptide mediates fusion of membrane-bounded organelles.

7. The mitofusin polypeptide of claim 6, wherein said membrane-bounded organelles are mitochondria.

8. A purified mitofusin polypeptide encoded by a nucleic acid that hybridizes under stringent conditions to the complementary sequence to SEQ ID NO:3.

9. The mitofusin polypeptide of claim 8, wherein said polypeptide mediates fusion of membrane-bounded organelles.

10. The mitofusin polypeptide of claim 9, wherein said membrane-bound organelles are mitochondria.

11. The purified polypeptide fragment of claim 4, wherein said fragment is immunogenic.

12. The purified polypeptide fragment of claim 4, wherein said fragment comprises a coiled coil domain.

13. The purified polypeptide fragment of claim 4, wherein said fragment comprises a GTPase domain.

14. The purified polypeptide fragment of claim 4, wherein said fragment comprises a transmembrane domain.

* * * * *

UNITED STATES PATENT AND TRADEMARK OFFICE
CERTIFICATE OF CORRECTION

PATENT NO. : 6,127,159
DATED : October 3, 2000
INVENTOR(S) : Fuller et al.

It is certified that error appears in the above-identified patent and that said Letters Patent is hereby corrected as shown below:

Please insert the following statement in the first paragraph on the first page of the specification:

--This invention was made with Government support under contract HD29194 awarded by the National Institutes of Health. The Government has certain rights in this invention.--

Signed and Sealed this

Eighth Day of May, 2001

NICHOLAS P. GODICI

*Attest:*

*Attesting Officer*          Acting Director of the United States Patent and Trademark Office

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 2399 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

GAGCAAAACA ACATCTACAG TTGCCTATAT TTCATAAATA AATTTGTTAA CATTTTTGTA      60

ATATCTAATC ATAATGGCGG AATCTGACTC CGGAGAAAGT ACGTCGTCGG TGTCCTCGTT     120

TATATCCTCA TCGTCGTCTT CGCGATTAAG TGAGTTTGTG GACGCAAAGA CAGAACTGCA     180

GGATATATAT CACGATTTGA GTAATTACCT GTCCAATTTC CTAACCATTT TGGAGGAGAC     240

TGTCCTCTTA AAAGATCGAC AAATGCTGGA GCACCTGTGC GCCTTCTCCA GCAGGGTGGA     300

GGCCATTGCA AAGGTTCTTT CACGTGATCG AATGAAGGTG GCATTTTTTG GACGCACCTC     360

AAATGGAAAA AGTGCCGTGA TCAATGCACT TCTGCATGAA AAAATCCTGC CCAGCGCCAT     420

GGGCCATACC ACCAGCTGTT TTTGTCAAGT GCAAGCTAAT GGCTCGAATG AAACCGAGCA     480

CGTAAAGGTC GAGCAGGAGG ATGAGCATAT GGAACTGAGT GCCCTAAGCC AACTGGCCAG     540

TGCACATTCT CCTGGGGCCC TAAAACCCTC AACTCTGCTG CAGGTCAATA TGGCCAAGAA     600

CCGTTGCTCG ATATTGGATT ACGATGTGGT TTTGATGGAT ACACCTGGAG TGGATGTAAC     660

AGCGCAACTG GACGATTGCC TAGATAGCTA CTGCATGGAT GCGGATGTTT TCATTCTAGT     720

TCTCAACGCC GAGTCCACTG TTTCGCGCGT GGAAAGGCAG TTCTTCAAGG ACGTGGCATC     780

CAAACTCTCG CGTCCAAATC TCTTTATACT CAACAATCGA TGGGATAAGG CCAGCAGTCT     840

GGAGCCGGAA ATGGAGCAGA AGGTAAAGGA TCAGCATATG GAACGTTGCG TTAACCTGCT     900

```
CGTGGATGAA TTAGGTGTTT ATTCAACTGC ACAGGAAGCG TGGGAAAGGA TCTATCATGT      960

TTCAGCACTG GAGGCATTGC ATATAAGGAA TGGTCAGATT ACGAATCCCT CGGGACAAAC     1020

CCAACAGCGA TATCAGGAGT TTCTGCGTTT CGAAAATGAT TTTTCGAATT GCCTCGCGGT     1080

GTCAGCGTTA AAAACCAAAT TTGGTCCACA CTTGCTAAGT GCGCAGAAGA TTTTAAACCA     1140

GTTAAAATCA ACTCTGATAT GCCCTTTCAT AGAGAAAGTA AGTCGTCTTA TCGATGAGAA     1200

TAAGGAGAGA AGAGCTAACT TGAATGCCGA AATAGAGGAC TGGTTAATAC TAATGCAAGA     1260

GGATAGAGAA GCGCTTCAAT ATTGTTTCGA AGAACTGACT GAAATGACAC AAAGAGTAGG     1320

TCGGTGCGTT TTGAGCGACC AGATAAAAAC GTTAATACCC TCGTCTGTGC TATCATTCTC     1380

GCAACCATTT CACCCGGAAT TCCCAGCACA AATAGGCCAG TACCAACGCT CGTTATGTGC     1440

CCATTTGGAT AAACTTCTTG AAGATCGTGT CCTTCAATGT CTCTCCATAC CCCTACAAAG     1500

AGAAATATTA GATATAGAGA AAGAAATTGG GCTTCCGATC GCCGAGAACT CTTGCGATTG     1560

GCAACTAATC TACGGCCTGG ATTGCCAATC CTATATGAGT GACTTTCAGC CAGATCTTAG     1620

GTTTCGATTT TCTTTGGGTT TTACTGCCCT GTGGCATCGT CTTGAAGGCA ACCTACCGTT     1680

GCACGCAAGT CCATTTCGAA TTCAAAAGTT ACAAAATGGT CACAAGAAAT GTTCGCCCCT     1740

GCCACCTTTA GTTAACGGAA ACCATTGGCA GATGCTGGAA TCTTTGGTGA AGTCTAAAGG     1800

TAGCTTGGGC ACCGTTTTAC TGAGCGCCAT GGCCATCCGT TCGTTCAACT GGCCAATTGT     1860

ATTGATCCTT GGTGGGCTCG TCGGATCCTT TTACATCTAC GAGTACGCCG CTTGGACAAC     1920

TGCCGCCCAA GAGCGAAGTT TCAAGAGCCA GTACGCCAGG CTCTTGCAAC AACGTCTGCG     1980

GTCGGATGTG CAGCAAACTG TTAGCGGTTT TGAGCTCCAG TTGCGACAGC ACCTGGCAAC     2040

GGTCCGAAAT TGCTGGGAAG CCCAGTCCAA TGAGACACTG AATGACCTGA ACGTAAGGAC     2100

CGCGGAGCTG ACCAAACAAA TACAATCGAT GGAGGTGTTG CAGCTCAGCC TGAAGAAGTT     2160

TCGGGACAAG GGACAGCTGC TGGCCAGTCG GTTGGGAGAC TTTCAAGAGA CCTACTTGAC     2220

CAAGAGCTGA CAATTATGAG GGGGGTTACA ACAAATTCTA AATGTTCTTA ATAGTTTTAA     2280

TTTATTTTTG GTTACCTAAT TAAGTATTGT AATTCCGTTA TGTTACTTAG AAATTTTGTA     2340

TGTATTTGGT TGAATATTTT AAAATATTAA ACGATTGGTC TTCACTACTT TAAAGTTAA      2399
```

(2) INFORMATION FOR SEQ ID NO:2:

(i) SEQUENCE CHARACTERISTICS:
        (A) LENGTH: 718 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Glu Ser Asp Ser Gly Glu Ser Thr Ser Ser Val Ser Ser Phe
 1               5                  10                  15

Ile Ser Ser Ser Ser Ser Arg Leu Ser Glu Phe Val Asp Ala Lys
                20                  25                  30

Thr Glu Leu Gln Asp Ile Tyr His Asp Leu Ser Asn Tyr Leu Ser Asn
         35                  40                  45

Phe Leu Thr Ile Leu Glu Glu Thr Val Leu Leu Lys Asp Arg Gln Met
     50                  55                  60

Leu Glu His Leu Cys Ala Phe Ser Ser Arg Val Glu Ala Ile Ala Lys
 65                  70                  75                  80

Val Leu Ser Arg Asp Arg Met Lys Val Ala Phe Phe Gly Arg Thr Ser
```

```
                        85                  90                  95
Asn Gly Lys Ser Ala Val Ile Asn Ala Leu Leu His Glu Lys Ile Leu
                100                 105                 110

Pro Ser Ala Met Gly His Thr Thr Ser Cys Phe Cys Gln Val Gln Ala
                115                 120                 125

Asn Gly Ser Asn Glu Thr Glu His Val Lys Val Glu Gln Glu Asp Glu
            130                 135                 140

His Met Glu Leu Ser Ala Leu Ser Gln Leu Ala Ser Ala His Ser Pro
145                 150                 155                 160

Gly Ala Leu Lys Pro Ser Thr Leu Leu Gln Val Asn Met Ala Lys Asn
                165                 170                 175

Arg Cys Ser Ile Leu Asp Tyr Asp Val Val Leu Met Asp Thr Pro Gly
            180                 185                 190

Val Asp Val Thr Ala Gln Leu Asp Asp Cys Leu Asp Ser Tyr Cys Met
            195                 200                 205

Asp Ala Asp Val Phe Ile Leu Val Leu Asn Ala Glu Ser Thr Val Ser
210                 215                 220

Arg Val Glu Arg Gln Phe Phe Lys Asp Val Ala Ser Lys Leu Ser Arg
225                 230                 235                 240

Pro Asn Leu Phe Ile Leu Asn Asn Arg Trp Asp Lys Ala Ser Ser Leu
                245                 250                 255

Glu Pro Glu Met Glu Gln Lys Val Lys Asp Gln His Met Glu Arg Cys
            260                 265                 270

Val Asn Leu Leu Val Asp Glu Leu Gly Val Tyr Ser Thr Ala Gln Glu
            275                 280                 285

Ala Trp Glu Arg Ile Tyr His Val Ser Ala Leu Glu Ala Leu His Ile
290                 295                 300

Arg Asn Gly Gln Ile Thr Asn Pro Ser Gly Gln Thr Gln Gln Arg Tyr
305                 310                 315                 320

Gln Glu Phe Leu Arg Phe Glu Asn Asp Phe Ser Asn Cys Leu Ala Val
                325                 330                 335

Ser Ala Leu Lys Thr Lys Phe Gly Pro His Leu Leu Ser Ala Gln Lys
            340                 345                 350

Ile Leu Asn Gln Leu Lys Ser Thr Leu Ile Cys Pro Phe Ile Glu Lys
            355                 360                 365

Val Ser Arg Leu Ile Asp Glu Asn Lys Glu Arg Arg Ala Asn Leu Asn
370                 375                 380

Ala Glu Ile Glu Asp Trp Leu Ile Leu Met Gln Glu Asp Arg Glu Ala
385                 390                 395                 400

Leu Gln Tyr Cys Phe Glu Glu Leu Thr Glu Met Thr Gln Arg Val Gly
                405                 410                 415

Arg Cys Val Leu Ser Asp Gln Ile Lys Thr Leu Ile Pro Ser Ser Val
            420                 425                 430

Leu Ser Phe Ser Gln Pro Phe His Pro Glu Phe Pro Ala Gln Ile Gly
            435                 440                 445

Gln Tyr Gln Arg Ser Leu Cys Ala His Leu Asp Lys Leu Leu Glu Asp
            450                 455                 460

Arg Val Leu Gln Cys Leu Ser Ile Pro Leu Gln Arg Glu Ile Leu Asp
465                 470                 475                 480

Ile Glu Lys Glu Ile Gly Leu Pro Ile Ala Glu Asn Ser Cys Asp Trp
                485                 490                 495

Gln Leu Ile Tyr Gly Leu Asp Cys Gln Ser Tyr Met Ser Asp Phe Gln
            500                 505                 510
```

```
Pro Asp Leu Arg Phe Arg Phe Ser Leu Gly Phe Thr Ala Leu Trp His
            515                 520                 525

Arg Leu Glu Gly Asn Leu Pro Leu His Ala Ser Pro Phe Arg Ile Gln
        530                 535                 540

Lys Leu Gln Asn Gly His Lys Lys Cys Ser Pro Leu Pro Pro Leu Val
545                 550                 555                 560

Asn Gly Asn His Trp Gln Met Leu Glu Ser Leu Val Lys Ser Lys Gly
                565                 570                 575

Ser Leu Gly Thr Val Leu Leu Ser Ala Met Ala Ile Arg Ser Phe Asn
            580                 585                 590

Trp Pro Ile Val Leu Ile Leu Gly Gly Leu Val Gly Ser Phe Tyr Ile
        595                 600                 605

Tyr Glu Tyr Ala Ala Trp Thr Thr Ala Ala Gln Glu Arg Ser Phe Lys
    610                 615                 620

Ser Gln Tyr Ala Arg Leu Leu Gln Gln Arg Leu Arg Ser Asp Val Gln
625                 630                 635                 640

Gln Thr Val Ser Gly Phe Glu Leu Gln Leu Arg Gln His Leu Ala Thr
                645                 650                 655

Val Arg Asn Cys Trp Glu Ala Gln Ser Asn Glu Thr Leu Asn Asp Leu
            660                 665                 670

Asn Val Arg Thr Ala Glu Leu Thr Lys Gln Ile Gln Ser Met Glu Val
        675                 680                 685

Leu Gln Leu Ser Leu Lys Lys Phe Arg Asp Lys Gly Gln Leu Leu Ala
    690                 695                 700

Ser Arg Leu Gly Asp Phe Gln Glu Thr Tyr Leu Thr Lys Ser
705                 710                 715

(2) INFORMATION FOR SEQ ID NO:3:

(i) SEQUENCE CHARACTERISTICS:
        (A) LENGTH: 2176 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

ACAGTTAATC AACTGGCCCA TGCCCTTCAC ATGGACAAAG ATTTGAAAGC TGGCTGTCTT      60

GTACGTGTGT TTTGCCCAAA AGCAAAATGT GCCCTCTTGA GAGATGACCT GGTGTTAGTA     120

GACAGTCCAG GCACAGATGT CACTACAGAG CTGGATAGCT GGATTGATAA GTTTTGCCTA     180

GATGCTGATG TCTTTGTTTT GGTCGCAAAC TCTGAATCAA CACTAATGAA TACGGAAAAA     240

CACTTTTTTC ACAAGGTGAA TGAGCGGCTT TCCAAGCCTA ATATTTTCAT TCTCAATAAT     300

CGTTGGGATG CCTCTGCATC AGAGCCAGAA TATATGGAAG ACGTACGCAG ACAGCACATG     360

GAAAGATGCC TGCATTTCTT GGTGGAGGAG CTCAAAGTTG TAAATGCTTT AGAAGCACAG     420

AATCGTATCT TCTTTGTTTC AGCAAAGGAA GTTCTTAGTG CTAGAAAGCA AAAAGCACAG     480

GGGATGCCAG AAAGTGGTGT GGCACTTGCT GAAGGATTTC ATGCAAGATT ACAGGAATTT     540

CAGAATTTTG AACAAATCTT TGAGGAGTGT ATCTCGCAGT CAGCAGTGAA ACAAAGTTC      600

GAACAGCACA CTATCAGAGC TAAACAGATA CTAGCTACTG TGAAAACATA ATGGATTCA      660

GTAAACCTGG CAGCTGAAGA TAAAAGGCAT TATTCAGTGG AAGAGAGGGA AGACCAAATT     720

GATAGACTGG ACTTTATTCG AAACCAGATG AACCTTTTAA CACTGGATGT TAAGAAAAAA     780
```

```
ATCAAGGAGG TTACCGAGGA GGTGCCAAAC AAAGTTTCAT GTGCAATGAC AGATGAAATT      840

TGTCGACTGT CTGTTTTGGT TGATGAATTT TGTTCAGAGT TTCATCCTAA TCCAGATGTA      900

TTAAAAATAT ATAAAAGTCT CCCTAGATCT TTAGCTTCTA CTCCCACTGC TCCTACCACT      960

CCAGCAACGC CAGATAATGC ATCACAGGAA GAACTCATGA TTACATTAGT AACAGGATTG     1020

GCGTCCGTTA CATCTAGAAC TTCTATGGGC ATCATTATTG TTGGAGGAGT GATTTGGAAA     1080

ACTATAGGCT GGAAACTCCT ATCTGTTTCA TTAACTATGT ATGGAGCTTT GTATCTTTAT     1140

GAAAGACTGA GCTGGACCAC CCATGCCAAG GAGCGAGCCT TTAAACAGCA GTTTGTAAAC     1200

TATGCAACTG AAAAACTGAG GATGATTGTT AGCTCCACGA GTGCAAACTG CAGTCACCAA     1260

GTAAAACAAC AAATAGCTAC CACTTTTGCT CGCCTGTGCC AACAAGTTGA TATTACCCAC     1320

AAACAGCTGG AAGAAGAAAT TGCTAGATTA CCCAAAGAAA TAGATCAGTT GGAGAAAATC     1380

CAAAACAATT CAAAGCTCTT AAGAAATAAA GCTGTTCAAC TTGAAAATGA GCTGGAGAAT     1440

TTTACTAAGC AGTTTCTACC TTCAAGCAAT GAAGAATCCT AACAATAGAG ATTGCTTTGG     1500

TGACCATGAT AGGAGGAAAC GAAACTTGTA AGATTGGAAC AGTTGTTATT TTTATGAAAT     1560

TACTTTAAAT ATGAATTGTA CTATCTGTAC CTAAATAGCA AAGCCCTGTG TAGATTCTGG     1620

TAATGATCTG TCTCAGGGTA TGTGTATTTT TGAAGAGTGT TATGTCCTTA GTTTTAATTT     1680

TGAGTAAAGA AAAGGCTAAA ATCATGAATT AGTTACAAGC AACAGTACCA ACTTATGTGA     1740

CCCCTGAGGG GTGGGGCTGT GAGCTCTTAA TTTGTTTTTG ATTCTGAAAA ACTCTGCTTC     1800

CTGGCATCCA GGAGTTAGAG ATTGAGCCTT TCATCTTCTT TCTCAACACT AGTTTTTGAT     1860

GCTTTCTTTC ATGGGAATAG TCACTTTTTT ATTTAGTAAA ATCGCATTGC TGGAACCACC     1920

CGCCGCATCT CTTCTTCACG GCGCCTGCGC TCTTCCTCCT GCCTGAGCTC CAGTTGCTTT     1980

CGTTTTTGCA CCTCTTGGTT GTGCGGCTCT TCCATCCTCC GAAGTTCTTC TTGGCGCCTC     2040

ATCAAATCCT GTCTCATTAG CATGACCTGG TGCTCATGGC GTGCAGCTTC CATCTCCATC     2100

TCCAGCTTCT CACGAGCCTA GCAGAAGGGG GTGGTGTCTC CAACCCCCCA GCACTGAGGA     2160

AGAGCGGGGC TCTTCT                                                    2176
```

(2) INFORMATION FOR SEQ ID NO:4:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Thr Val Asn Gln Leu Ala His Ala Leu His Met Asp Lys Asp Leu Lys
 1               5                  10                  15

Ala Gly Cys Leu Val Arg Val Phe Cys Pro Lys Ala Lys Cys Ala Leu
                20                  25                  30

Leu Arg Asp Asp Leu Val Leu Val Asp Ser Pro Gly Thr Asp Val Thr
            35                  40                  45

Thr Glu Leu Asp Ser Trp Ile Asp Lys Phe Cys Leu Asp Ala Asp Val
        50                  55                  60

Phe Val Leu Val Ala Asn Ser Glu Ser Thr Leu Met Asn Thr Glu Lys
65                  70                  75                  80

His Phe Phe His Lys Val Asn Glu Arg Leu Ser Lys Pro Asn Ile Phe
                85                  90                  95
```

Ile Leu Asn Asn Arg Trp Asp Ala Ser Ala Ser Glu Pro Glu Tyr Met
            100                 105                 110

Glu Asp Val Arg Arg Gln His Met Glu Arg Cys Leu His Phe Leu Val
            115                 120                 125

Glu Glu Leu Lys Val Val Asn Ala Leu Glu Ala Gln Asn Arg Ile Phe
            130                 135                 140

Phe Val Ser Ala Lys Glu Val Leu Ser Ala Arg Lys Gln Lys Ala Gln
145                 150                 155                 160

Gly Met Pro Glu Ser Gly Val Ala Leu Ala Glu Gly Phe His Ala Arg
                165                 170                 175

Leu Gln Glu Phe Gln Asn Phe Glu Gln Ile Phe Glu Glu Cys Ile Ser
            180                 185                 190

Gln Ser Ala Val Lys Thr Lys Phe Glu Gln His Thr Ile Arg Ala Lys
            195                 200                 205

Gln Ile Leu Ala Thr Val Lys Asn Ile Met Asp Ser Val Asn Leu Ala
            210                 215                 220

Ala Glu Asp Lys Arg His Tyr Ser Val Glu Glu Arg Glu Asp Gln Ile
225                 230                 235                 240

Asp Arg Leu Asp Phe Ile Arg Asn Gln Met Asn Leu Leu Thr Leu Asp
                245                 250                 255

Val Lys Lys Lys Ile Lys Glu Val Thr Glu Val Pro Asn Lys Val
            260                 265                 270

Ser Cys Ala Met Thr Asp Glu Ile Cys Arg Leu Ser Val Leu Val Asp
            275                 280                 285

Glu Phe Cys Ser Glu Phe His Pro Asn Pro Asp Val Leu Lys Ile Tyr
290                 295                 300

Lys Ser Leu Pro Arg Ser Leu Ala Ser Thr Pro Thr Ala Pro Thr Thr
305                 310                 315                 320

Pro Ala Thr Pro Asp Asn Ala Ser Gln Glu Glu Leu Met Ile Thr Leu
                325                 330                 335

Val Thr Gly Leu Ala Ser Val Thr Ser Arg Thr Ser Met Gly Ile Ile
            340                 345                 350

Ile Val Gly Gly Val Ile Trp Lys Thr Ile Gly Trp Lys Leu Leu Ser
            355                 360                 365

Val Ser Leu Thr Met Tyr Gly Ala Leu Tyr Leu Tyr Glu Arg Leu Ser
            370                 375                 380

Trp Thr Thr His Ala Lys Glu Arg Ala Phe Lys Gln Gln Phe Val Asn
385                 390                 395                 400

Tyr Ala Thr Glu Lys Leu Arg Met Ile Val Ser Ser Thr Ser Ala Asn
                405                 410                 415

Cys Ser His Gln Val Lys Gln Ile Ala Thr Thr Phe Ala Arg Leu
            420                 425                 430

Cys Gln Gln Val Asp Ile Thr His Lys Gln Leu Glu Glu Glu Ile Ala
            435                 440                 445

Arg Leu Pro Lys Glu Ile Asp Gln Leu Glu Lys Ile Gln Asn Asn Ser
450                 455                 460

Lys Leu Leu Arg Asn Lys Ala Val Gln Leu Glu Asn Glu Leu Glu Asn
465                 470                 475                 480

Phe Thr Lys Gln Phe Leu Pro Ser Ser Asn Glu Glu Ser
                485                 490

(2) INFORMATION FOR SEQ ID NO:5:

(i) SEQUENCE CHARACTERISTICS:

```
            (A) LENGTH: 27 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:5:

ACCTCAAATG GAACTAGTGC CGTGATC                                           27

(2) INFORMATION FOR SEQ ID NO:6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:6:

TACTCAACAA TCTATGGGAT AAG                                               23
```